(12) United States Patent
Sakai et al.

(10) Patent No.: US 8,163,490 B2
(45) Date of Patent: Apr. 24, 2012

(54) METHOD OF ANALYZING METHYLATED DNA

(75) Inventors: Ayako Sakai, Kobe (JP); Masahiro Kajita, Kobe (JP); Hideki Ishihara, Miki (JP)

(73) Assignee: Sysmex Corporation, Hyogo (JP)

( * ) Notice: Subject to any disclaimer, the term of this patent is extended or adjusted under 35 U.S.C. 154(b) by 280 days.

(21) Appl. No.: 12/403,167

(22) Filed: Mar. 12, 2009

(65) Prior Publication Data

US 2009/0246784 A1    Oct. 1, 2009

(30) Foreign Application Priority Data

Mar. 27, 2008    (JP) .................. 2008-083806

(51) Int. Cl.
*C12Q 1/68* (2006.01)
*C12P 19/34* (2006.01)

(52) U.S. Cl. ................ 435/6.12; 435/6.1; 435/6.11

(58) Field of Classification Search .............. None
See application file for complete search history.

(56) References Cited

PUBLICATIONS

Ilana Keshet. et al., "Evidence for an Instructive Mechanism of de novo methylation in cancer cells," Nature Genetics, Feb. 2006; vol. 38, No. 2 , pp. 149-153.
Hayashi.H et al., High-resolution mapping of DNA methylation in human genome using oligonucleotide tiling array, Human Genetics, Jan. 2007; 120(5): pp. 701-711.

*Primary Examiner* — Young J Kim
(74) *Attorney, Agent, or Firm* — Sughrue Mion, PLLC

(57) ABSTRACT

The present invention provides a method of analyzing methylated DNA, comprising steps of: (A) treating a DNA-containing sample with a restriction enzyme to obtain a sample containing a DNA fragment; (B) concentrating methylated DNA contained in the sample obtained in step (A) to obtain a methylated DNA concentrate; (C) subjecting the methylated DNA concentrate obtained in step (B) and a primer set to nucleic acid amplification reaction, wherein the primer set performs the nucleic acid amplification reaction in step (C) by using a template DNA which does not have a CpG site; (D) detecting an amplification product obtained in step (C); (E) judging whether the methylated DNA concentrate obtained in step (B) is appropriate as a sample for detection of methylated DNA, on the basis of the detection result of the amplification product in step (D); and (F) analyzing the methylated DNA contained in the methylated DNA concentrate.

15 Claims, 13 Drawing Sheets

Fig. 7

GAPDH-seq1_CpG

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1 | ○ | ● | ● | ● | ○ | ○ | ● | ● | ● | ○ | ○ | ● | ● | ● | ● | ● | ● |
| 2 | ● | ● | ● | ● | ● | ● | ○ | ● | ○ | ○ | ● | ● | ● | ● | ● | ● | ● |
| 3 | ● | ● | ● | ● | ● | ○ | ○ | ● | ● | ● | ● | ● | ● | ● | ● | ● | ● |

MCF7

Fig. 8

GAPDH-seq2_CpG

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1 | ● | ● | ● | ● | ● | ● | ○ | ○ | ○ | ● | ● | ○ | ○ | ○ |
| 2 | ● | ● | ● | ● | ● | ● | ○ | ● | ● | ● | ○ | ● | ○ | ○ |
| 3 | ○ | ● | ● | ● | ● | ● | ○ | ● | ○ | ● | ○ | ○ | ● | ○ |

MCF7

1         2         3

(a)

(b)

1        2        3

(a)

(b)

1 2 3

(a)

(b)

METHOD OF ANALYZING METHYLATED DNA

BACKGROUND OF THE INVENTION

1. Field of the Invention

The present invention relates to a method of analyzing methylated DNA. The present invention relates in particular to a method of analyzing methylated DNA, a primer set, a method of judging a reliability of a step of concentrating methylated DNA, a method of detecting non-methylated DNA in a methylated DNA concentrate, a method of calculating a concentration rate of methylated DNA, and a method of evaluating a purity of a methylated DNA concentrate.

2. Description of the Related Art

Methylation of a CpG site in DNA significantly influences gene expression. For example, abnormalities in methylation of DNA are known to participate in the onset of diseases, for example, in the expression of genes related to malignant transformation of cells. Accordingly, the methylation of DNA in various genes is comprehensively studied in various genes in order to develop diagnostic and therapeutic methods for diseases such as cancer.

In analysis of the methylation of DNA, methylated DNA is concentrated for example by immunoprecipitation of methylated DNA with an anti-methylated cytosine antibody, an anti-methylated cytidine antibody or a methylated DNA-binding protein. Thereafter, profiling of DNA contained in the resulting concentrate is conducted. In analysis of such DNA methylation, the efficiency of analysis may be decreased when non-methylated DNA is contained in the methylated DNA concentrate. For example, in the immunoprecipitation of methylated DNA, non-methylated DNA may be bound or adsorbed nonspecifically to an anti-methylated cytosine antibody, an anti-methylated cytidine antibody, a methylated DNA-binding protein, or bead. Consequently, the presence or absence, or the content, of non-methylated DNA in the methylated DNA concentrate is confirmed in such analysis of DNA methylation.

Detection of non-methylated DNA in a methylated DNA concentrate is conducted by using, as an indicator, a housekeeping gene that has been estimated to be non-methylated. In a method described in Ilana Keshet. et al., Nature Genetics, February 2006; 38(2): 149-53, a glyceraldehyde-3-phosphate dehydrogenase (hereinafter referred to as "GAPDH") gene is used as an indicator of non-methylated DNA. In this method, an amount of a methylated DNA concentrate concentrated by immunoprecipitation of methylated DNA is determined by standardization with the detected GAPDH gene. In a method described in Hayashi H. et al., Human Genetics, January 2007; 120(5):701-11, a GAPDH gene and β-actin gene are used as non-methylated DNAs. In the method described in this Non-Patent Document 2, the concentration rate of methylated DNA is evaluated by using, as an indicator, the absence of detection of the GAPDH gene and β-actin gene in the methylated DNA concentrate obtained by immunoprecipitation of methylated DNA.

However, there are cases where cytosine at a CpG site in each of the GAPDH gene and β-actin gene has been actually methylated. It follows that when housekeeping genes such as GAPDH gene and β-actin gene are used as the indicator, non-methylated DNA in a methylated DNA concentrate may not be accurately detected. Accordingly, there are cases where evaluation of the concentration rate and purity of a methylated DNA concentrate, or judgment of the reliability of its concentrating step, cannot be accurately conducted.

The state of the housekeeping gene used as an indicator can be confirmed by determining its DNA sequence after treatment with hydrogen sulfite, in order to secure the accuracy of the concentration rate and the like of a methylated DNA concentrate. In this case, however, the operation of confirming the state of methylation is troublesome and time-consuming. As a result, there is a problem that methylated DNA cannot be efficiently and easily analyzed by using a methylated DNA concentrate.

SUMMARY OF THE INVENTION

The scope of the present invention is defined solely by the appended claims, and is not affected to any degree by the statements within this summary.

One object of the present invention is to provide a method of analyzing methylated DNA wherein methylated DNA can be easily and efficiently analyzed. Another object of the present invention is to provide a primer set capable of accurately and easily detecting the presence or absence, or an amount, of non-methylated DNA in a methylated DNA concentrate. Still another object of the present invention is to provide a method of judging a reliability of an analysis result of methylated DNA, wherein the reliability of the analysis result of methylated DNA can be easily and accurately judged. Still another object of the present invention is to provide a method of detecting non-methylated DNA in a methylated DNA concentrate, wherein the non-methylated DNA in a methylated DNA concentrate can be easily and accurately detected. Still another object of the present invention to provide a method of calculating a concentration rate of methylated DNA, wherein the concentration rate of non-methylated DNA by various methods of concentrating methylated DNA can be easily and accurately calculated. Still another object of the present invention is to provide a method of evaluating a purity of a methylated DNA concentrate, wherein the purity of a methylated DNA concentrate by various methods of concentrating methylated DNA can be easily and accurately evaluated.

The method of analyzing methylated DNA according to the present invention demonstrates an excellent effect of enabling methylated DNA to be easily and efficiently analyzed. The primer set of the present invention demonstrates an excellent effect of enabling the presence or absence or the amount of methylated DNA in a methylated DNA concentrate to be easily and accurately detected. The method of detecting a reliability of an analysis result of methylated DNA according to the present invention demonstrates an excellent effect of enabling the reliability of an analysis result of methylated DNA to be easily and accurately judged. The method of detecting non-methylated DNA in a methylated DNA concentrate according to the present invention demonstrates an excellent effect of enabling non-methylated DNA in a methylated DNA concentrate to be easily and accurately detected. The method of calculating a concentration rate of methylated DNA according to the present invention demonstrates an excellent effect of enabling the concentration rate of methylated DNA by various methods of concentrating methylated DNA to be easily and accurately calculated. The method of evaluating a purity of a methylated DNA concentrate according to the present invention demonstrates an excellent effect of enabling the purity of a methylated DNA concentrate by various methods of concentrating methylated DNA to be easily and accurately evaluated.

BRIEF DESCRIPTION OF THE DRAWINGS

FIG. 7 is a schematic diagram of a methylated state of CpG regions contained in a DNA sequence of a GAPDH gene amplified with a GAPDH-seq1 primer set.

FIG. 8 is a schematic diagram of a methylated state of CpG regions contained in a DNA sequence of a GAPDH gene amplified with a GAPDH-seq2 primer set.

DETAILED DESCRIPTION OF THE INVENTION

A major feature of the present invention lies in a primer set using, as a template, a DNA fragment which does not have a CpG site among DNA fragments obtained by fragmenting DNA contained in a DNA-containing sample with a restriction enzyme. This primer set can be used in nucleic acid amplification reaction using, as a template, a DNA fragment which does not have a CpG site, contained in a methylated DNA concentrate, thereby enabling easy and accurate detection of non-methylated DNA. Hereinafter, the method of detecting non-methylated DNA in a methylated DNA concentrate, and the primer set, according to the present invention will be described.

The detection method of the present invention comprises steps of (A) treating a DNA-containing sample with a restriction enzyme to obtain a sample containing a DNA fragment, (B) concentrating methylated DNA contained in the sample obtained in step (A) to obtain a methylated DNA concentrate, (C) subjecting the methylated DNA concentrate obtained in step (B) and a primer set to nucleic acid amplification reaction, wherein the primer set performs the nucleic acid amplification reaction by using, as a template, a DNA fragment which does not have a CpG site among DNA fragments obtained in step (A), and (D) detecting the amplification product obtained in step (C).

The detection method of the present invention makes use of a primer set using, as a template, a DNA fragment which does not have a CpG site among DNA fragments obtained by treating DNA in a DNA-containing sample with a restriction enzyme. The DNA fragment serving as a template does not have a CpG site. Accordingly, the region of this DNA fragment in genomic DNA in the living body such as human body is not methylated. Accordingly, the DNA fragment which does not have a CpG site can be used as an indicator of the presence of non-methylated DNA in a methylated DNA concentrate in order to accurately detect non-methylated DNA in the methylated DNA concentrate. In the detection method of the present invention, therefore, nucleic acid amplification reaction using a methylated DNA concentrate and the primer set is carried out and an amplification product obtained by the nucleic acid amplification reaction is detected, whereby non-methylated DNA in the methylated DNA concentrate can be accurately and easily detected.

In this specification, methylated DNA refers to DNA wherein cytosine at a CpG site is methylated into 5-methyl-cytosine. Further, in this specification, non-methylated DNA refers to DNA wherein cytosine at a CpG site is not methylated. The CpG site is a cytosine/guanine dinucleotide site which comprises 5'-CpG-3' present in the genome and which is subjected to methylation. Such CpG site is involved in regulation of gene expression, in cancer, and in imprinting.

Figure 1:
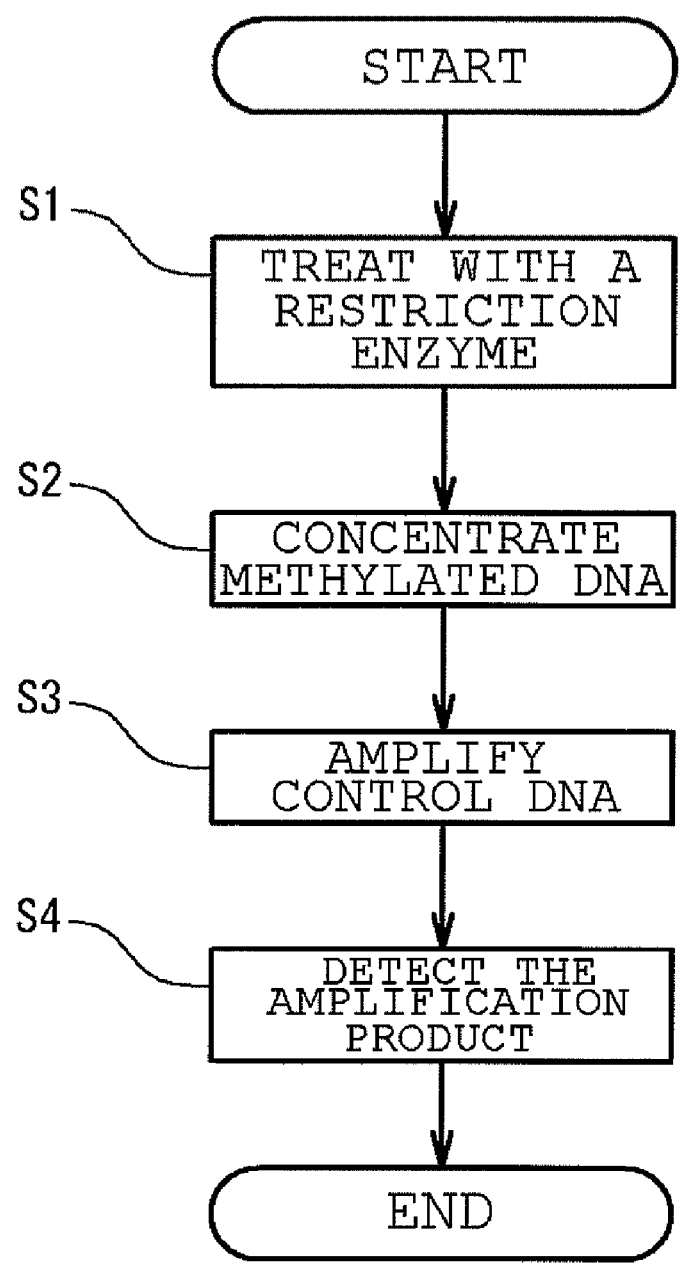
FIG. 1 is a flowchart showing one embodiment of the detection method of the present invention.

FIG. 1 shows a flowchart showing one embodiment of the detection method of the present invention.

In the detection method of the present invention, a DNA-containing sample is first treated with a restrictive enzyme to obtain a sample containing a DNA fragment (step S1). Step S1 corresponds to step (A) described above.

The DNA-containing sample may be a sample containing a DNA derived from the living body. The sample includes, for example, a sample containing a DNA prepared from tissues or cells collected from humans. Particularly, a sample containing a DNA prepared from cancer tissues or cancer cells collected from cancer patients to be subjected to analysis of methylated DNA is preferable.

The DNA can also be extracted from tissues or cells by methods known in the art. For example, tissues or cells collected from the living body are lysed with a surfactant and then deproteinized with phenol or the like thereby yielding the DNA. Alternatively, the DNA may be extracted with a commercial DNA extraction kit, or the like. The extracted DNA may be dissolved in water or a suitable buffer.

The restriction enzyme is preferably a restriction enzyme recognizing 4 to 6 bases. In the present invention, the restriction enzyme recognizing 4 to 6 bases can be used to make the DNA into fragments each having a size suitable for serving as a template in nucleic acid amplification.

The restriction enzyme may be a restriction enzyme that recognizes a nucleotide sequence which does not have a CpG site to cleave its cleavage site therein. Specific examples of the restriction enzyme include MseI, AluI, and XbaI. The restriction enzymes may be used singly or as a mixture of two or more thereof. Treatment of DNA with the restriction enzyme is conducted under reaction conditions adapted to the restriction enzyme used.

Then, the methylated DNA contained in the resulting sample is concentrated to yield a methylated DNA concentrate (step S2). Step S2 corresponds to step (B) described above.

The methylated DNA is concentrated with an anti-methylated cytosine antibody, an anti-methylated cytidine antibody or a methylated DNA-binding protein. The method of concentrating the methylated DNA includes, for example:

(1) a method of immunoprecipitating the methylated DNA with an anti-methylated cytosine antibody or an anti-methylated cytidine antibody thereby recovering the methylated DNA (MeDIP method);

(2) a method of immunoprecipitating the methylated DNA with a methylated DNA-binding protein and an antibody against the methylated DNA-binding protein thereby recovering the methylated DNA; and (3) a method of binding the methylated DNA to a histidine tag-fused methylated DNA-binding protein and then recovering, with a nickel-immobilized carrier, the histidine tag-fused methylated DNA-binding protein to which the methylated DNA has been bound, thereby recovering the methylated DNA.

The anti-methylated cytosine antibody and the anti-methylated cytidine antibody may be antibodies that bind specifically to methylated cytosine (5-methylcytosine) or methylated cytidine in the DNA. These antibodies can be prepared for example by using methylated cytidine, or DNA containing the methylated cytosine in its molecule, as an antigen with which animals are to be immunized by conventional methods. Alternatively, commercially available anti-methylated cytosine antibodies and anti-methylated cytidine antibodies may be also used.

Thereafter, the methylated DNA concentrate thus obtained is subjected to nucleic acid amplification reaction with a primer set using, as template, a DNA fragment which does not have a CpG site among DNA fragments obtained by treating the DNA-containing sample with a restriction enzyme (step S3). The operation in step S3 corresponds to step (C) described above. Nucleic acid corresponding to the whole or a part of the DNA fragment which does not have a CpG site is thereby amplified. The control DNA in step S3 in FIG. 1 refers to the DNA fragment which does not have a CpG site among DNA fragments obtained by treating the DNA-containing sample with a restriction enzyme.

The nucleic acid amplification method of performing nucleic acid amplification reaction includes polymerase chain reaction (PCR), strand displacement reaction, ligase chain reaction, and transcription amplification. In particular, real-time PCR that is one kind of polymerase chain reaction is desirable from the viewpoint of rapid and easy quantification of an amplification product. In real-time PCR, an amplification product DNA is monitored in real time, and the DNA is quantified in an exponential amplification range. Accordingly, the DNA can be accurately quantified on the basis of amplification kinetics in the polymerase chain reaction. Real-time PCR includes, for example, a method of using a fluorescent intercalator (intercalator method) and a method of using a probe (for example, a TaqMan probe, and a cycling probe) comprising a fluorescent dye-labeled oligonucleotide specific for a sequence of an amplification product (probe method). Among them, the intercalator method is preferable from the viewpoint of easy detection and quantification of the amplification product. In the intercalator method, an intercalator is a substance that binds to a double-stranded DNA synthesized by polymerase chain reaction and emits fluorescence upon irradiation with an exciting light. In the intercalator method, fluorescence intensity based on the fluorescence of the intercalator that is bound to the amplification product obtained as a double-stranded DNA can be detected to monitor the amount of the amplification product formed. The intercalator includes, for example, SYBR® green manufactured by Molecular Probe Inc.

Then, the amplification product obtained in the nucleic acid amplification reaction is detected (step S4). Step S4 corresponds to step (D) described above. In the detection method of the present invention, detection of the amplification product serves as an indicator of the presence of non-methylated DNA in the methylated DNA concentrate.

Detection of the amplification product can be confirmed by methods known in the art, for example, by conventional agarose gel electrophoresis, a detection method of hybridizing the amplification product with a labeled probe, or a method of detecting a turbidity of a byproduct generated by nucleic acid amplification.

Now, the primer set of the present invention is described.

According to the primer set of the present invention, nucleic acid amplification reaction can be carried out by using a DNA fragment which does not have a CpG site as a template in the nucleic acid amplification reaction. Accordingly, non-methylated DNA in the methylated DNA concentrate can be accurately detected by using, as an indicator of the non-methylated DNA, the amplification product obtained by the nucleic acid amplification reaction using the primer set of the present invention. According to the primer set of the present invention, non-methylated DNA can be detected by merely performing the nucleic acid amplification reaction. Consequently, non-methylated DNA in the methylated DNA concentrate can be easily detected.

The primer set of the present invention contains a primer that hybridizes with one DNA strand of a DNA fragment which does not have a CpG site among DNA fragments obtained by treating DNA with a restriction enzyme and a primer that hybridizes with a complementary strand of the DNA strand. That is, the target sequence to be hybridized by each of the primers is present in a nucleotide sequence of the DNA fragment which does not have a CpG site. The "complementary strand" refers to a DNA strand that forms a pair with the other DNA chain in a double-stranded DNA.

When the primer set of the present invention is a primer set used in polymerase chain reaction (PCR), the difference in Tm value between its forward and reverse primers is preferably within 2° C. The percentage of guanine and cytosine in the nucleotide sequence of each of the primers in the primer set is desirably 40 to 60%. It is preferable that the nucleotide sequence of one primer in the primer set do not contain 4 or more consecutive guanine residues. Each primer in the primer set is preferably 17 to 25 nucleotides in length. The annealing temperature of each primer in the primer set in PCR is set preferably at a temperature near Tm.

For example, when human genomic DNA is treated with MseI, the resulting DNA fragment which does not have a CpG site includes, for example, DNA fragments having a nucleotide sequence of SEQ ID NO: 1, SEQ ID NO: 2 or SEQ ID NO: 3. These DNA fragments do not contain a CpG site in their nucleotide sequence and are thus preferable as the indicator of nom-methylated DNA in human genomic DNA.

The primer set using, as a template, a DNA fragment having the nucleotide sequence set forth in SEQ ID NO: 1, SEQ ID NO: 2 or SEQ ID NO: 3 includes:

(1) a primer set composed of a combination of a primer comprising a nucleotide sequence set forth in SEQ ID NO: 4 (CGF1-F: 5'-GGAGGAGTCAAGAGAAGTTGGAAGC-3') and a primer comprising a nucleotide sequence set forth in SEQ ID NO: 5 (CGF1-Rv: 5'-CCCACACTCCATTTCCATTCCTC-3'), (2) a primer set composed of a combination of a primer comprising a nucleotide sequence set forth in SEQ ID NO: 6 (CGF2-F: 5'-GGGTACTTTGCCAATATAGCCATGC-3') and a primer comprising a nucleotide sequence set forth in SEQ ID NO: 7 (CGF2-Rv: 5'-TGGCTAAGTGGGAGG-GAGAACAG-3'), and (3) a primer set composed of a combination of a primer comprising a nucleotide sequence set forth in SEQ ID NO: 8 (CGF3-F: 5'-GGATGGGAGACACCTGGTTCA-3') and a primer comprising a nucleotide sequence set forth in SEQ ID NO: 9 (CGF3-Rv: 5'-GGATGGACCAGCTGCTTTG- TACTC-3'). According to these primer sets, amplification products suitable as the indicator of non-methylated DNA can be obtained.

The primer set can be designed by known methods, depending on the type of nucleic acid amplification method of performing nucleic acid amplification reaction. Primer design software for designing primers is also commercially available. The primer design software includes GENETYX (trade name) manufactured by Software Kaihatsu Co., Ltd. and primer 3 (trade name) manufactured by Software Kaihatsu Co., Ltd.

In the detection method of the present invention, non-methylated DNA in a methylated DNA concentrate can be easily and accurately detected. Accordingly, whether a sample for detection of methylated DNA that is a methylated DNA concentrate is suitable for analysis of methylated DNA can be easily and accurately judged by the detection method of the present invention. Consequently, the time-consuming and troublesome operation of confirming the methylated state of a housekeeping gene is eliminated. As a result, it is made possible to analyze methylated DNA easily and efficiently by using a methylated DNA concentrate. Accordingly, the present invention encompasses a method of analyzing methylated DNA.

The analysis method of the present invention comprises steps of:
(A) treating a DNA-containing sample with a restriction enzyme to obtain a sample containing a DNA fragment;
(B) concentrating methylated DNA contained in the sample obtained in step (A) to obtain a methylated DNA concentrate;
(C) subjecting the methylated DNA concentrate obtained in step (B) and a primer set to nucleic acid amplification reaction, wherein the primer set performs the nucleic acid amplification reaction by using, as a template, a DNA fragment which does not have a CpG site among DNA fragments obtained in step (A);
(D) detecting the amplification product obtained in step (C);
(E) judging whether the methylated DNA concentrate obtained in step (B) is appropriate as a sample for detection of methylated DNA, on the basis of the detection result of the amplification product in step (D); and
(F) analyzing the methylated DNA contained in the methylated DNA concentrate.

When it is judged in step (E) that the methylated DNA concentrate obtained in step (B) is appropriate as a sample for detection of methylated DNA, step (F) is preferably a step of analyzing the methylated DNA contained in the methylated DNA concentrate. In this case, methylated DNA can be accurately analyzed by using an appropriate sample for detection of methylated DNA. By eliminating an inappropriate sample for detection of methylated DNA from analytes, methylated DNA can be more efficiently analyzed.

Figure 2:
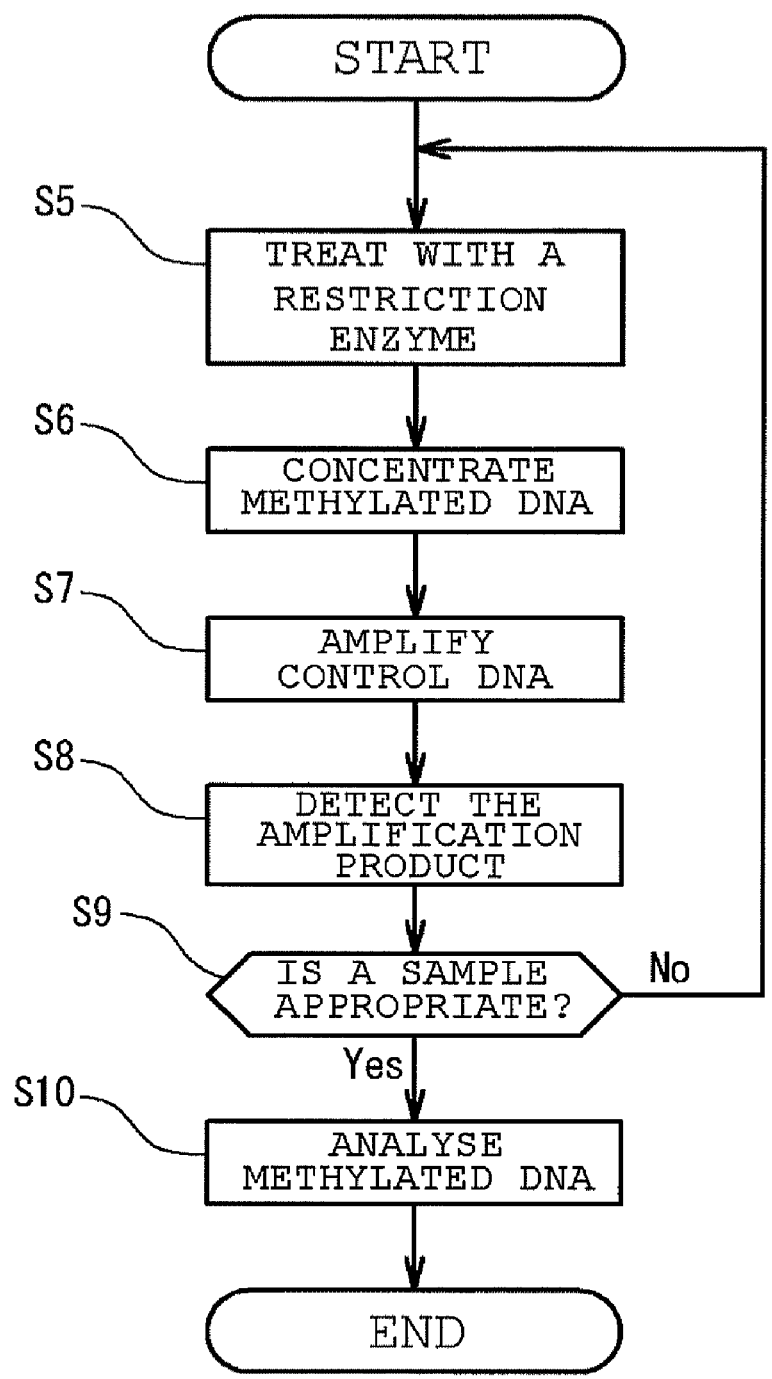
FIG. 2 is a flowchart showing one embodiment of the analysis method of the present invention.

A flowchart showing one embodiment of the analysis method of the present invention is shown in FIG. 2. The flowchart in FIG. 2 shows an embodiment of analyzing methylated DNA in step (F) when the methylated DNA concentrate is appropriate as a sample for detection of methylated DNA.

Steps (A) to (D) in the analysis method of the present invention are the same as steps (A) to (D) in the detection method of the present invention. That is, the same operations as in steps S1 to S4 shown in FIG. 1 are conducted in steps S5 to S8 shown in FIG. 2.

In the analysis method of the present invention, whether the resulting methylated DNA concentrate is appropriate as a sample for detection of methylated DNA is judged in step (E) (step S9), based on the detection result of the amplification product. When the amplification product is detected in excess, the methylated DNA concentrate obtained in step S6 (step (B)) can be judged to be inappropriate as a sample for detection of methylated DNA. On the other hand, when the amplification product is very little or not detected, the methylated DNA concentrate obtained in step S6 (step (B)) can be judged to be appropriate as a sample for detection of methylated DNA.

For example, when an amount of the control DNA contained in a methylated DNA concentrate, as determined by the real-time PCR, is higher than a predetermined amount, this methylated DNA concentrate can be judged to be inappropriate as a sample for detection of methylated DNA. On the other hand, when the amount of the control DNA contained in a methylated DNA concentrate is not higher than a predetermined amount, this methylated DNA concentrate can be judged to be appropriate as a sample for detection of methylated DNA. The predetermined amount is empirically established appropriately in consideration of the total amount of DNA contained in the methylated DNA concentrate as well as conditions for analysis of methylated DNA.

When a primer set using, as a template, methylated DNA among DNA fragments described later is further used in the analysis method of the present invention, whether the methylated DNA concentrate is appropriate as a sample for detection of methylated DNA can also be judged from the concentration rate or purity of methylated DNA. That is, when the concentration rate or purify is low, the methylated DNA concentrate can be judged to be inappropriate as a sample for detection of methylated DNA. On the other hand, when the concentration rate or purify is high, the methylated DNA concentrate can be judged to be appropriate as a sample for detection of methylated DNA.

When it is judged in step S9 (step (E)) that the methylated DNA concentrate is inappropriate as a sample for detection of methylated DNA, the process is returned to step S5 (step (A)) and the operation of acquiring a methylated DNA concentrate may be conducted again.

Then, when the methylated DNA concentrate is judged to be appropriate as a sample for detection of methylated DNA, methylated DNA contained in the methylated DNA concentrate is analyzed (step S10). That is, step S10 corresponds to step (F) in the analysis method of the present invention.

The method carried out in analysis of methylated DNA is not particularly limited as long as it is a known analysis method wherein the methylated DNA concentrate is used as a sample for detection of methylated DNA. The method of analyzing methylated DNA includes, for example, a method of using DNA chips on which DNA of a disease-related gene, DNA of a transcription factor, DNA of an expression regulation factor, DNA of a promoter region, and the like are immobilized. The DNA chips are preferably tiling arrays wherein nucleotide sequences picked out at regular intervals from decoded genome data in gene expression information are fixed as detection probes in the form of tiles.

As described above, the description of steps S9 and S10 explains a flow where methylated DNA is analyzed in step (F) when the methylated DNA concentrate is appropriate as a sample for detection of methylated DNA. Accordingly, the analysis method of the present invention is not limited to the flow shown in the flowchart in FIG. 2.

For example, the analysis method of the present invention includes a flow of performing step 9 after step 10. That is, the methylated DNA contained in the methylated DNA concentrate is analyzed, and it is then judged whether the methylated DNA concentrate is appropriate as a sample for detection of methylated DNA. When the methylated DNA concentrate is judged to be appropriate as a sample for detection of methylated DNA, analysis of the methylated DNA is finished. On the other hand, when the methylated DNA concentrate is judged to be inappropriate as a sample for detection of methylated DNA, the process is returned to step S5 (step (A)) and the operation of acquiring a methylated DNA concentrate is conducted again.

In the detection method of the present invention, non-methylated DNA in the methylated DNA concentrate can be easily and accurately detected. Accordingly, the reliability of an analysis result of methylated DNA can be easily and accurately judged by using the detection method of the present invention. Therefore, the present invention encompasses a method of judging a reliability of an analysis result of methylated DNA.

The method of judging a reliability of an analysis result of methylated DNA according to the present invention comprises steps of:
(A) treating a DNA-containing sample with a restriction enzyme to obtain a sample containing a DNA fragment;
(B) concentrating methylated DNA contained in the sample obtained in step (A) to obtain a methylated DNA concentrate;
(C) subjecting the methylated DNA concentrate obtained in step (B) and a primer set to nucleic acid amplification reaction, wherein the primer set performs the nucleic acid amplification reaction by using, as a template, a fragment which does not have a CpG site among DNA fragments obtained in step (A);
(D) detecting the amplification product obtained in step (C);
(G) analyzing methylated DNA contained in the methylated DNA concentrate obtained in step (B); and
(H) judging the reliability of the analysis result of the methylated DNA in step (G), on the basis of the detection result of the amplification product in step (D).

Figure 3:
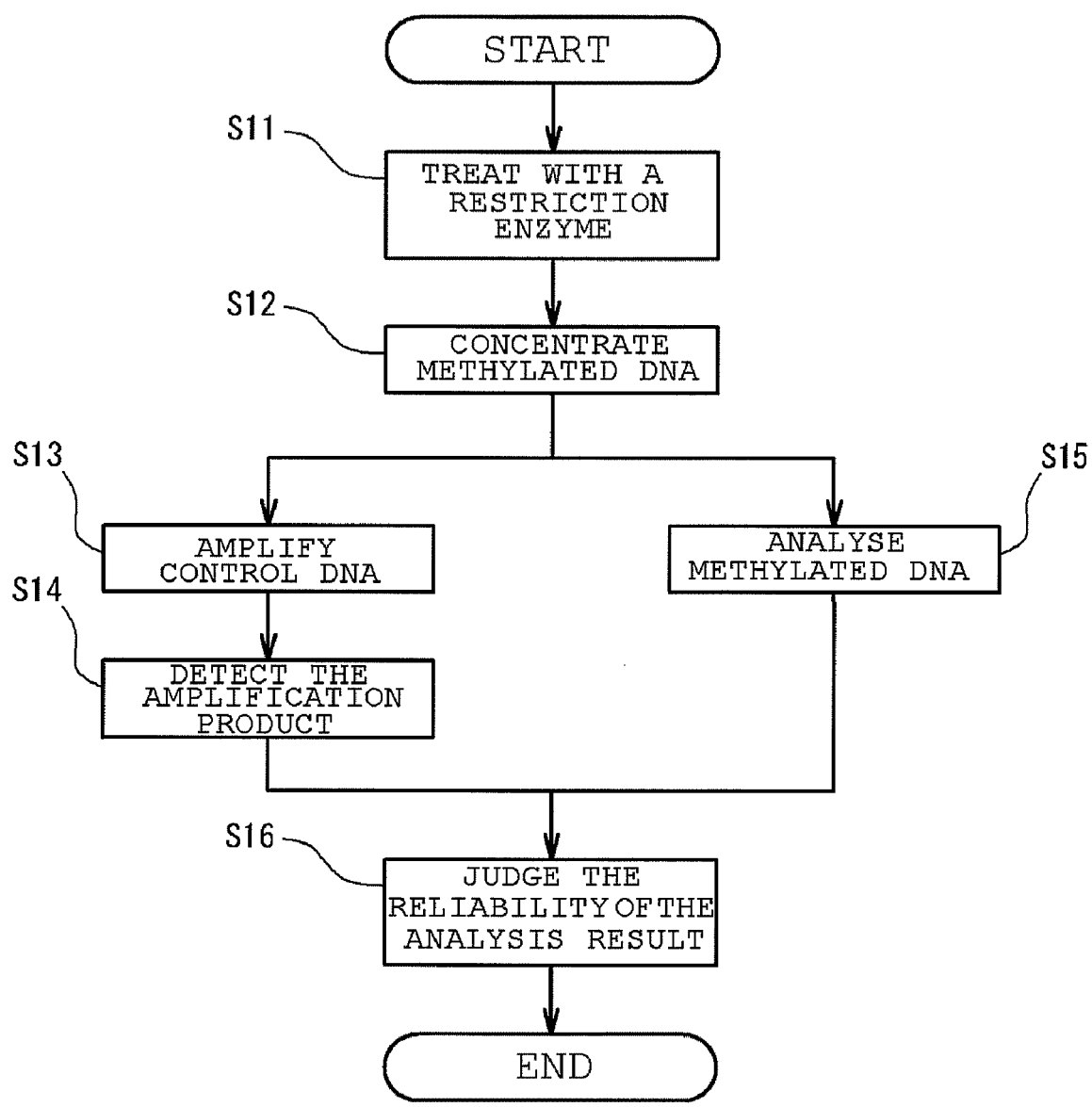
FIG. 3 is a flowchart showing one embodiment of the judgment method of the present invention.

FIG. 3 shows a flowchart showing one embodiment of the judgment method of the present invention.

The operations in steps (A) to (D) in the judgment method of the present invention are the same as in steps (A) to (D) in the detection method described above. That is, the same operations as in steps S1 to S4 shown in FIG. 1 are carried out in steps S11 to S14 shown in FIG. 3.

In the judgment method of the present invention, a part of the methylated DNA concentrate obtained in step S12 (step (B)) is used in analysis of methylated DNA (step S15). That is, step S15 corresponds to step (G) in the judgment step of the present invention. The analysis of methylated DNA is carried out by the same method as in analysis of methylated DNA in step S10 (step (F)) in the analysis method of the present invention.

A part of the remaining methylated DNA concentrate is used in amplification of control DNA in step S13 (step (C)) and in detection of the amplification product in step S14 (step (D)).

After detection of the amplification product, the reliability of the analysis result of methylated DNA is judged on the basis of the detection result of the amplification product (step S16)). That is, step S15 corresponds to step (H) in the judgment method of the present invention. The reliability of the analysis result of methylated DNA in step S15 (step (H)) can be judged by the same method as in judging whether the sample for detection of methylated DNA in step S9 (step (E)) is appropriate or not. That is, when the amplification product is detected in excess, the analysis result of methylated DNA in step S15 (step (G)) can be judged to be low in reliability. On the other hand, when the amplification product is very little or not detected, the analysis result can be judged to be high in reliability.

The concentration rate of methylated DNA can be calculated by using the primer set of the present invention and a primer set using, as a template, methylated DNA among DNA fragments obtained by treating a DNA-containing sample with a restriction enzyme. The present invention encompasses a method of calculating the concentration rate of methylated DNA.

The method of calculating of the concentration rate of methylated DNA according to the present invention comprises steps of:
(A) treating a DNA-containing sample with a restriction enzyme to obtain a sample containing DNA fragments;
(B) concentrating methylated DNA contained in the sample obtained in step (A) to obtain a methylated DNA concentrate;
(I) performing the following nucleic acid amplification reactions (i) to (iv):
(i) nucleic acid amplification reaction using the methylated DNA concentrate obtained in step (B) and a primer set using, as a template, a DNA fragment which does not have a CpG site among the DNA fragments described above;
(ii) nucleic acid amplification reaction using the methylated DNA concentrate obtained in step (B) and a primer set using, as a template, methylated DNA among the DNA fragments described above;
(iii) nucleic acid amplification reaction using the sample containing DNA fragments obtained in step (A) and a primer set using, as a template, a DNA fragment which does not have a CpG site among the DNA fragments described above; and
(iv) nucleic acid amplification reaction using the sample containing DNA fragments obtained in step (A) and a primer set using, as a template, methylated DNA among the DNA fragments described above;
(J) measuring the amount of the amplification product obtained in step (I); and
(K) calculating the concentration rate of the methylated DNA in step (B), on the basis of the amount of the amplification product measured in step (J).

Figure 4:
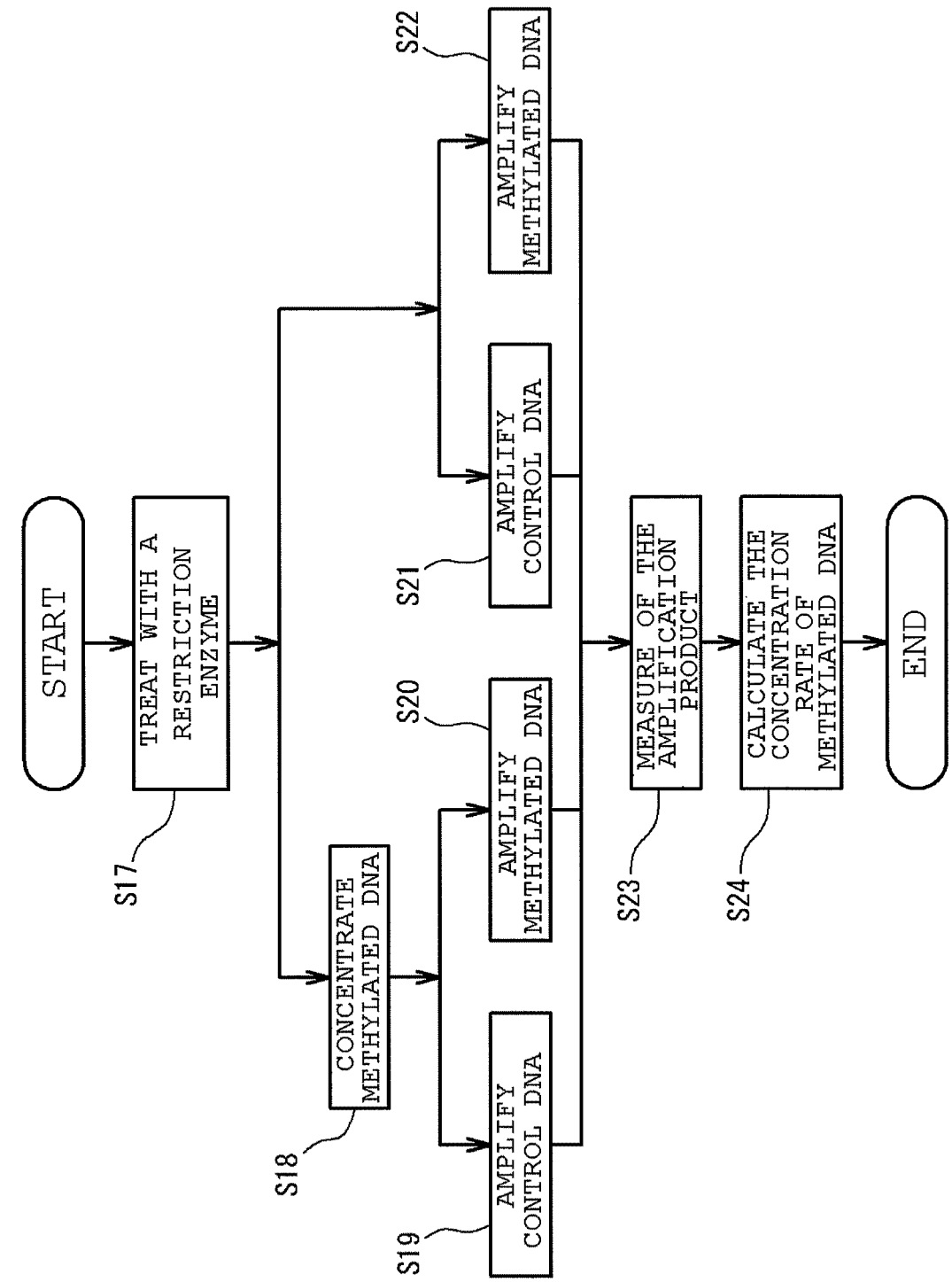
FIG. 4 is a flowchart showing one embodiment of the calculation method of the present invention.

FIG. 4 shows a flowchart showing one embodiment of the calculation method of the present invention.

The operations in steps (A) and (B) in the calculation method of the present invention are the same as in steps (A) and (B) in the detection method of the present invention. That is, the same operations as in steps S1 and S2 shown in FIG. 1 are conducted in steps S17 and S18 shown in FIG. 4.

In the method of calculating the concentration rate of methylated DNA according to the present invention, the nucleic acid amplification reactions (i) to (iv) described above are carried out in step (I) (steps S19 to S22). Step S19 refers to the nucleic acid amplification reaction (i), step S20 to the nucleic acid amplification reaction (ii), step S21 to the nucleic acid amplification reaction (iii), and step S22 to the nucleic acid amplification reaction (iv).

The nucleic acid amplification reaction can be carried out by known nucleic acid amplification methods capable of quantitatively determining the amount of the amplification product. Examples of such methods include real-time LAMP in addition to the real-time PCR. When nucleic acid is amplified by PCR or LAMP, the optical conditions (turbidity, absorbance, fluorescence intensity, and the like) of the reaction solution are changed with amplification of the nucleic acid. By measuring the optical condition in real time, the amount of the amplification product can be quantitatively determined.

When real-time LAMP is used, magnesium pyrophosphate is formed in a large mount as a byproduct with progress of nucleic acid amplification. This magnesium pyrophosphate is insoluble, and thus the reaction solution becomes turbid as magnesium pyrophosphate is increased. Accordingly, the turbidity (or absorbance) of the reaction solution can be measured optically in real time to quantitatively determine the amount of the amplification product. The intercalator method mentioned above can also be used in the real-time LAMP.

The primer set of the present invention can be used as a primer set in the nucleic acid amplification reactions (i) and (iii) (steps S19 and S21), which is used in amplifying a DNA fragment which does not have a CpG site among DNA fragments obtained by treating a DNA-containing sample with a restriction enzyme.

The primer set used in the nucleic acid amplification reactions (ii) and (iv) (steps S20 and S22) to amplify a DNA fragment containing a methylated cytosine among DNA fragments obtained by treating a DNA-containing sample with a restriction enzyme may be a primer set using, as a template, a DNA fragment containing a nucleotide sequence known to have cytosine methylated in DNA contained in the DNA-containing sample. Specific examples of such primer set include a primer set comprising a primer hybridizing with one DNA strand of a DNA fragment containing a methylated cytosine among DNA fragments obtained by treating DNA with a restriction enzyme and a primer hybridizing with a complementary strand of the DNA strand, in order to amplify the whole or a part of the DNA fragment containing a methylated cytosine methylated cytosine.

For example, when DNA contained in a DNA-containing sample is genomic DNA of MCF7 cell, the primer set capable of using, as a template, methylated DNA among DNA fragments obtained by treating the DNA-containing sample with a restriction enzyme includes a primer set containing a primer hybridizing with a nucleotide sequence, as a target sequence, in a promoter region of glutathione S-transferase pi gene (GSTP1). More specifically, when the genomic DNA of MCF7 cell is treated with MseI, the primer set includes a GSTP1 primer set comprising

```
GSTP1-F primer (5'-GAGGCCTTCGCTGGAGTT-3',
SEQ ID NO: 16)
and

GSTP1-R primer (5'-GTACTCACTGGTGGCGAAGA-3',
SEQ ID NO: 17).
```

In step (J), the amount of the resulting amplification product is measured (step S23).

As described above, the amount of the amplification product is determined by known methods depending on the nucleic acid amplification method used in step (I).

Thereafter, the concentration rate of methylated DNA is calculated in step (K) (step S24), based on the amount of the amplification product obtained by the nucleic acid amplification reactions (i) to (iv) described above. The amount of the amplification product obtained by the nucleic acid amplification reaction (i) serves as an indicator of the proportion of non-methylated DNA (control DNA) contained in the methylated DNA concentrate. The amount of the amplification product obtained by the nucleic acid amplification reaction (ii) serves as an indicator of the proportion of methylated DNA contained in the methylated DNA concentrate. The amount of the amplification product obtained by the nucleic acid amplification reaction (iii) serves as an indicator of the proportion of non-methylated DNA (control DNA) contained in the methylated DNA sample before concentration. The amount of the amplification product obtained by the nucleic acid amplification reaction (iv) serves as an indicator of the proportion of methylated DNA contained in the methylated DNA sample before concentration.

The concentration rate of methylated DNA can be calculated according to the following equation (1):

$$\text{Concentration rate of methylated DNA} = \frac{[\text{amount of amplification product obtained by nucleic acid amplification reaction (ii)}/\text{amount of amplification product obtained by nucleic acid amplification reaction (i)}]}{[\text{amount of amplification product obtained by nucleic acid amplification reaction (iv)}/\text{amount of amplification product obtained by nucleic acid amplification reaction (iii)}]} \quad (1)$$

By determining the amounts of the amplification products obtained by the nucleic acid amplification reactions (i) and (ii), the purity of the methylated DNA concentrate can also be evaluated. Accordingly, the present invention encompasses a method of evaluating a purity of a methylated DNA concentrate.

The method of evaluating a purity of a methylated DNA concentrate according to the present invention comprises steps of:

(A) treating a DNA-containing sample with a restriction enzyme to obtain a sample containing DNA fragments;

(B) concentrating methylated DNA contained in the sample obtained in step (A) to obtain a methylated DNA concentrate;

(L) performing the following nucleic acid amplification reactions (i) and (ii):

(i) nucleic acid amplification reaction using the methylated DNA concentrate obtained in step (B) and a primer set using, as a template, a DNA fragment which does not have a CpG site among the DNA fragments described above; and (ii) nucleic acid amplification reaction using the methylated DNA concentrate obtained in step (B) and a primer set using, as a template, methylated DNA among the DNA fragments described above;

(M) measuring the amount of the amplification product in step (L); and (N) evaluating the purity of the methylated DNA concentrate, on the basis of the amount of the amplification product measured in step (M).

Figure 5:
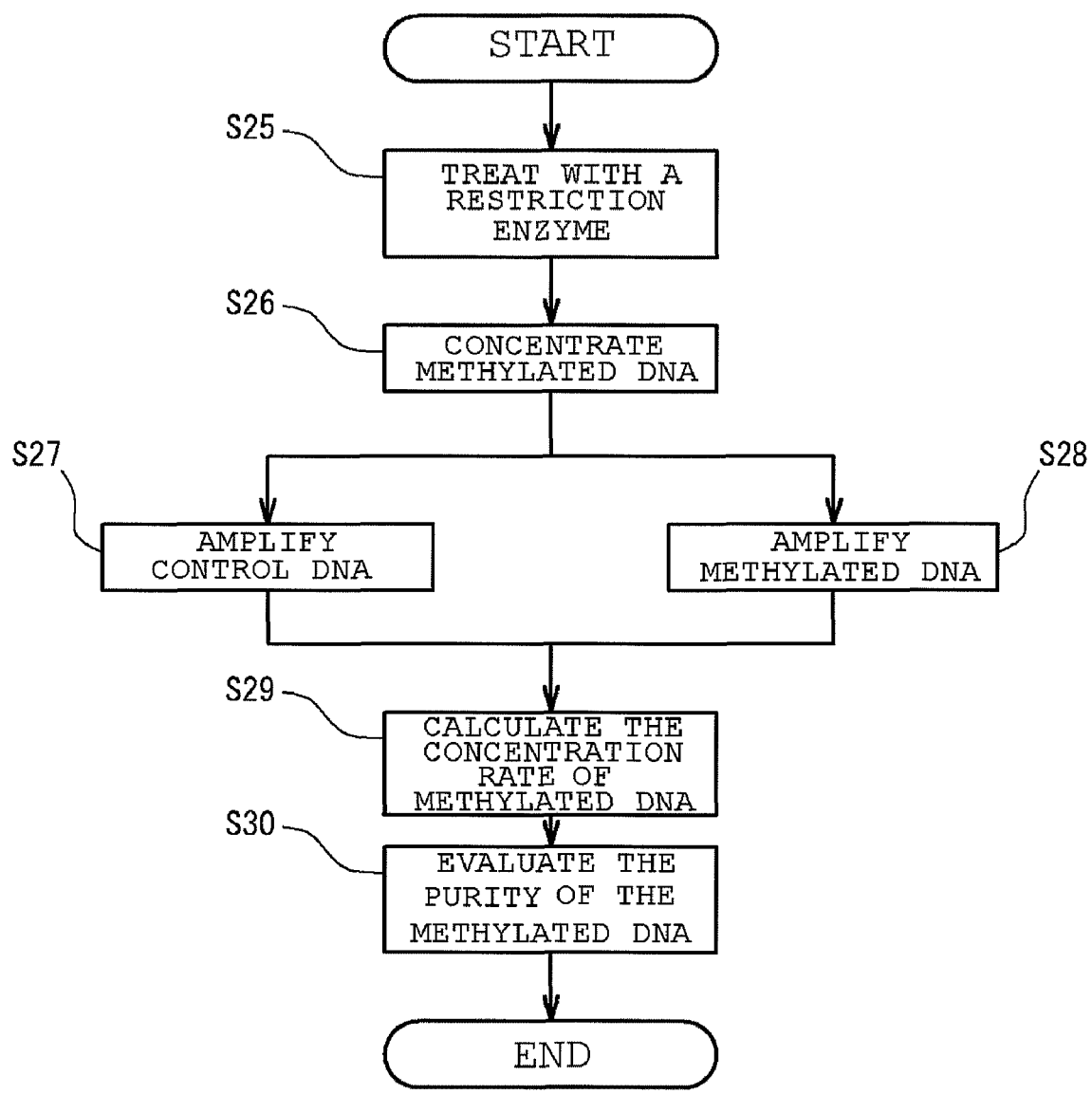
FIG. 5 is a flowchart showing one embodiment of the evaluation method of the present invention.

FIG. 5 shows a flowchart showing one embodiment of the evaluation method of the present invention.

The operations in steps (A) and (B) in the evaluation method of the present invention are the same as in steps (A) and (B) in the detection method of the present invention. That is, the same operations as in steps S1 and S2 shown in FIG. 1 are carried out in steps S25 and S26 shown in FIG. 5.

The operations in the nucleic acid amplification reactions (i) and (ii) in step (L) in the evaluation method of the present invention are the same as in the nucleic acid amplification reactions (i) and (ii) in step (I) in the calculation method of the present invention. That is, the same operations as in steps S19 and S20 shown in FIG. 4 are carried out in steps S27 and S28 shown in FIG. 5.

The amount of the amplification product in step (M) in the evaluation method of the present invention is the same as in measurement of the amount of the amplification product in step (J) in the calculation method of the present invention. That is, the same operation as in step S23 shown in FIG. 4 is carried out in step S29 shown in FIG. 5.

In the evaluation method of the present invention, the purity of the methylated DNA concentrate is evaluated (step S30), on the basis of the amounts of the amplification products obtained by the nucleic acid amplification reactions (i) and (ii) above. The purity of the methylated DNA concentrate can be evaluated by making a comparison between the amounts of the amplification products obtained in the nucleic acid amplification reactions (i) and (ii) above. For example, when a value obtained by dividing the amount of the amplification product obtained by the nucleic acid amplification reaction (ii) by the amount of the amplification product obtained by the nucleic acid amplification reaction (i) is higher, the purity of the methylated DNA concentrate can be evaluated to be higher, while when the value is lower, the purity of the methylated DNA concentrate can be evaluated to be lower.

EXAMPLES

Hereinafter, the present invention will be described in detail by reference to Examples, but the present invention is not limited to such Examples.

Example 1

Confirmation of Fragmentation of Genomic DNA by Treatment with a Restriction Enzyme One μg genomic DNA extracted from breast cancer cell strain MCF7 was incubated with a restriction enzyme at 37° C. for 2 hours to fragment the genomic DNA. The restriction enzyme or a combination of restriction enzymes in a buffer, used in fragmentation of the genomic DNA is as follows:
(1) MseI (manufactured by New England Bio Laboratory) in NEB buffer 2
(2) AluI (manufactured by New England Bio Laboratory) in NEB buffer 2
(3) combination of MseI and AluI in NEB buffer 2
(4) combination of MseI and XbaI (manufactured by New England Bio Laboratory) in NEB buffer 2
(5) combination of AluI and XbaI in NEB buffer 2

Figure 6:
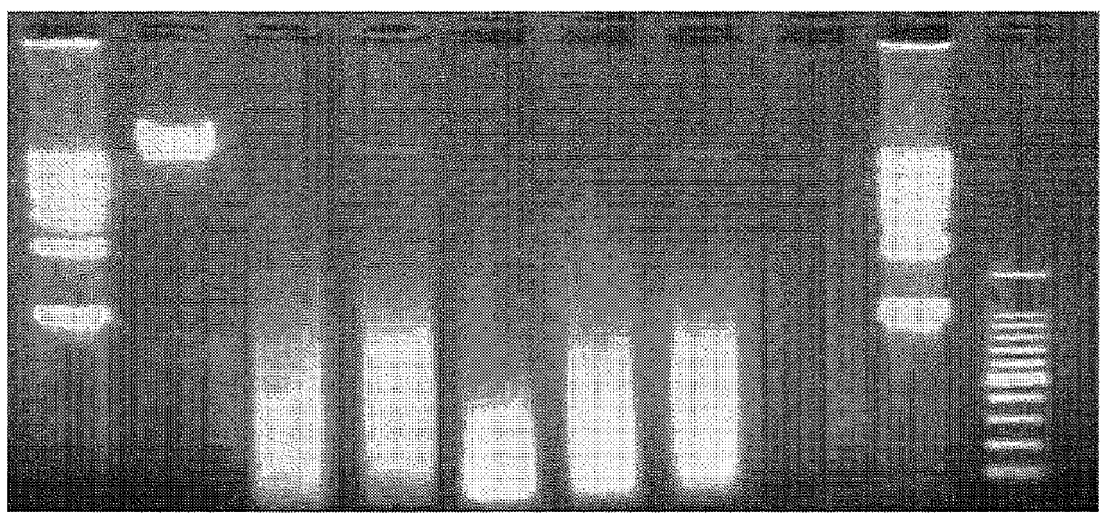
FIG. 6 is a photograph showing an electrophoresis pattern of DNA fragments.

The resulting DNA fragments were subjected to agarose gel electrophoresis to confirm the sizes of the DNA fragments. The results are shown in FIG. 6. FIG. 6 is a photograph showing electrophoresis patterns of the DNA fragments. In FIG. 6, lane 1 shows 1-kb ladder markers; lane 2, the untreated DNA; lane 3, DNA fragments after treatment with MseI; lane 4, DNA fragments after treatment with AluI; lane 5, DNA fragments after treatment with a combination of MseI and AluI; lane 6, DNA fragments after treatment with a combination of MseI and XbaI; lane 7, DNA fragments after treatment with a combination of AluI and XbaI; lane 8, 1-kb ladder markers; and lane 9, 100-bp ladder markers.

From the results shown in FIG. 6, it can be seen that because the DNA fragments obtained by treatment with any of the restriction enzymes are 300 to 1000 bp in size, DNA fragments having a size suitable for immunoprecipitation of methylated DNA are obtained.

Example 2

Analysis of Methylated DNA of GAPDH Gene

As a housekeeping gene, a GAPDH gene whose cytosine residues at CpG sites have been estimated to be non-methylated was examined for its methylated state.

Using a DNA extraction kit (trade name: QIAmp Blood Maxi Kit, manufactured by QIAGEN), genomic DNA was extracted from breast cancer cell strain MCF7. 400 μL of 0.3 M NaOH was added to 2 μg of the resulting genomic DNA followed by incubation at 37° C. for 10 minutes. Then, a product after incubation was treated with sodium hydrogen sulfite by adding 400 μL of 10 M sodium hydrogen sulfite and then incubating the sample at 70° C. for 40 minutes. The DNA contained in the resulting product was purified with a DNA purification kit (trade name: Qiaquick PCR purification kit, manufactured by QIAGEN) to prepare an analytical sample. This analytical sample was subjected to the following PCR.

0.12 μL of DNA polymerase (trade name: TaKaRa Ex Taq), 1.5 μL of buffer (trade name: 10× Ex Taq Buffer, manufactured by Takara Bio), 1.2 μL of 2.5 mM dNTP mixture, 0.6 μL of an aqueous forward primer solution (10 μM), 0.6 μL of an aqueous reverse primer solution (10 μM), and 9.98 μL of water were added to 1 μL of the analytical sample, to prepare a reaction solution for PCR. The reaction solution for PCR was used in PCR.

The used primer sets comprising forward and reverse primers are:
GAPDH-seq1 primer set comprising:

```
Forward primer: GAPDH-seq1-F:
5'-GAGATTTTTTTAAAATTAAGTGGGG-3'(SEQ ID NO: 10)
and Reverse primer: GAPDH-seq1-Rv:
5'-ATAAAAAAACCAATCCCCAAAAC-3'(SEQ ID NO: 11),
and GAPDH-seq2 primer set comprising:
Forward primer: GAPDH-seq2-F:
5'-TAGAGGGGTGATGTGGGGAGTA- 3'(SEQ ID NO: 12)
and Reverse primer: GAPDH-seq2-Rv:
5'-CTAACCCCAACCACATACCAAAA-3'(SEQ ID NO: 13).
```

The PCR with the GAPDH-seq1 primer set was conducted by incubation at 95° C. for 4.5 minutes followed by 40 cycles of the reaction, each cycle being carried out under conditions at 95° C. for 30 seconds, at 63° C. for 15 seconds and at 72° C. for 30 seconds, respectively. The PCR with the GAPDH-seq2 primer set was conducted by incubation at 95° C. for 4.5 minutes followed by 40 cycles of the reaction, each cycle being carried out under conditions at 95° C. for 30 seconds, at 66.7° C. for 15 seconds and at 72° C. for 30 seconds, respectively.

Using a cloning kit (trade name: TAcloning kit, manufactured by Invitrogen), the resulting PCR product was integrated into a vector attached to the cloning kit, to give a plasmid. The resulting plasmid and M13Rv primer were used to analyze the nucleotide sequence of the PCR product. The analysis results are shown in FIGS. 7 and 8.

FIG. 7 is a schematic diagram showing a methylated state of CpG regions contained in the DNA sequence of the GAPDH gene amplified with the GAPDH-seq1 primer set. In the DNA sequence of the GAPDH gene amplified with the GAPDH-seq1 primer set, there are 17 CpG sites. In the diagram, a white circle indicates a non-methylated CpG site, while a black circle indicates a methylated CpG site.

FIG. 8 is a schematic diagram showing a methylated state of CpG region contained in the DNA sequence of the GAPDH gene amplified with the GAPDH-seq2 primer set. In the DNA sequence of the GAPDH gene amplified with the GAPDH-seq2 primer set, there are 14 CpG sites. In the diagram, a white circle indicates a non-methylated CpG site, while a black circle indicates a methylated CpG site.

As is evident from FIGS. 7 and 8, it can be seen that cytosine residues in some of the CpG sites in the GAPDH gene are methylated. It was thereby revealed that depending on DNA as a subject to be analyzed for methylated DNA, the GAPDH gene that is a housekeeping gene may be inappropriate as an indicator of non-methylated DNA.

Example 3

Design of Primers for Detection of Non-Methylated DNA

A DNA fragment which does not have a CpG site obtained by treating the human genomic DNA with a restriction enzyme MseI was selected based on the nucleotide sequence of the human genomic DNA. As a result, DNA fragments represented by SEQ ID NOS: 1, 2 and 3 were selected.

Based on the nucleotide sequence of each selected DNA fragment, a primer set was designed for PCR with the DNA fragment as a template. Conditions for designing the primer are as follows:
(1) The difference in Tm between the forward primer and the reverse primer is within 2° C.
(2) The percentage of guanine and cytosine in the nucleotide sequence of the primer is 40 to 60%.
(3) The nucleotide sequence of the primer does not contain 4 or more consecutive guanine residues.
(4) The length of the primer is 17 to 25 bp.
(5) The annealing temperature is set at a temperature near Tm.

According to the design conditions described above, a primer set 1 using the DNA fragment represented by SEQ ID NO: 1 as a template, a primer set 2 using the DNA fragment represented by SEQ ID NO: 2 as a template and a primer set 3 using the DNA fragment represented by SEQ ID NO: 3 as a template were designed. Primers contained in each primer set are shown below.

```
Primer set 1:
CGF1-F primer (5'-GGAGGAGTCAAGAGAAGTTGGAAGC-3',
SEQ ID NO: 4)

CGF1-Rv primer (5'-CCCACACTCCATTTCCATTCCTC-3',
SEQ ID NO: 5)

Primer set 2:
CGF2-F primer (5'-GGGTACTTTGCCAATATAGCCATGC-3',
SEQ ID NO: 6)

CGF2-Rv primer (5'-TGGCTAAGTGGGAGGGAGAACAG-3',
SEQ ID NO: 7)

Primer set 3:
CGF3-F primer (5'-GGATGGGAGACACCTGGTTCA-3',
SEQ ID NO: 8)

CGF3-Rv primer (5'-GGATGGACCAGCTGCTTTGTACTC-3',
SEQ ID NO: 9)
```

(Design of Primers for Detection of Methylated DNA)

It is known that in the genomic DNA of MCF7 cell, a promoter region of glutathione S-transferase pi gene (GSTP1) is methylated. Accordingly, a GSTP1 primer set using, as a template, a DNA fragment containing the nucleotide sequence of the promoter region of GSTP1 was designed based on a DNA fragment obtained by treating the human genomic DNA with MseI as a restriction enzyme. Design conditions are the same as in design of the primers for detection of non-methylated DNA. Primers contained in the GSTP1 primer set are shown below.

```
GSTP1 primer set:
GSTP1-F primer (5'-GAGGCCTTCGCTGGAGTT-3',
SEQ ID NO: 16)

GSTP1-R primer (5'-GTACTCACTGGTGGCGAAGA-3',
SEQ ID NO: 17)
```

(Preparation of Analytical Sample)

4 µg of genomic DNA of breast cancer cell strain MCF7 and restriction enzyme MseI (manufactured by New England Laboratory) were incubated overnight at 37° C. to obtain a sample containing DNA fragments of 300 to 1000 bp. The resulting sample containing DNA fragments was thermally denatured by incubation at 95° C. for 10 minutes to give a preparative sample. The preparative sample for use in PCR described later was also prepared in the same manner.

68 µL of buffer (trade name: ChIP dilution buffer, manufactured by Upstate Inc.) and 302 µL of Protein G beads (trade name: Protein G Sepharose beads, manufactured by GE Healthcare) were added to the resulting preparative sample to give a mixture which was then incubated at 4° C. under stirring for 1 hour. Thereafter, a supernatant of the resulting mixture was recovered.

An anti-methylated cytidine antibody was added to the resulting supernatant, and the resulting mixture was incubated overnight at 4° C. under stirring, thereby immunoprecipitating methylated DNA.

Thereafter, an immunoprecipitation assay kit (trade name: Chromatin Immunoprecipitation Assay Kit, manufactured by Upstate Inc.) and Protein G beads (trade name: Protein G Sepharose beads, manufactured by GE Healthcare) were used to recover a DNA-antibody complex after immunoprecipitation, and the DNA was recovered from the complex.

Proteinase K (manufactured by Sigma) was added at a final concentration of 1 mg/mL to the recovered DNA-containing sample, and the resulting mixture was incubated at 50° C. for 1 hour. Thereafter, the DNA was purified from the resulting mixture by using a DNA purification kit (trade name: Qiaquick PCR purification kit, manufactured by QIAGEN), to give an analytical sample. This analytical sample was used in the following PCR. A sample obtained by the same manner as described above except that a mouse IgG antibody was used in place of the anti-methylated cytidine antibody was used as a control sample.

(PCR Using Each Primer Set)

12.5 µL of a PCR reagent (trade name: 2× fast Start SYBR Green Master Mix, manufactured by Roche Diagnostics), 1 µL of an aqueous forward primer solution (10 µM), 1 µL of an aqueous reverse primer solution (10 µM) and 9.5 µL water were added to 1 µL of the analytical sample, to prepare a reaction solution for PCR. The reaction solution for PCR was used in PCR. As controls, the preparative sample and the control sample were used in place of the analytical sample, to prepare reaction solutions for PCR which were then subjected to PCR.

The aqueous forward primer solution and the aqueous reverse primer solution contained the forward primer and reverse primer of the primer set 1, the primer set 2, the primer set 3 or the GSTP1 primer set.

PCR was conducted by incubation at 95° C. for 10 minutes and then 45 cycles of the reaction, each cycle being carried out under conditions at 95° C. for 30 seconds, at 66° C. for 15 seconds and at 72° C. for 30 seconds respectively, followed by the reaction carried out under conditions at 95° C. for 1 minute, at 66° C. for 30 seconds and at 95° C. for 30 seconds.

Detection of Amplified Nucleic Acid by Agarose Gel Electrophoresis

The nucleic acid amplified with PCR was detected by agarose gel electrophoresis. A photograph showing electrophoresis patterns after PCR using the primer set 1, the primer set 2, the primer set 3 and the GSTP1 primer set is shown in FIG. 9.

Figure 9:
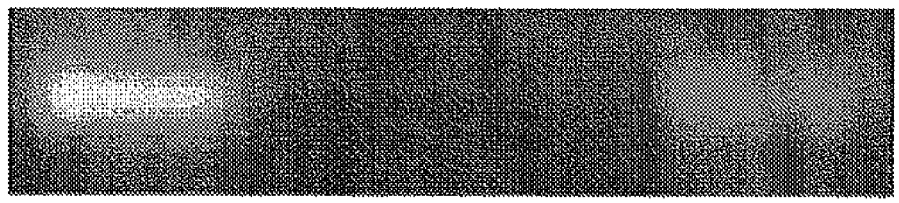
FIG. 9 is a photograph showing electrophoresis patterns of products after PCR when a primer set 1, a primer set 2, a primer set 3 and a GSTP1 primer set were used respectively.
Figure 9:
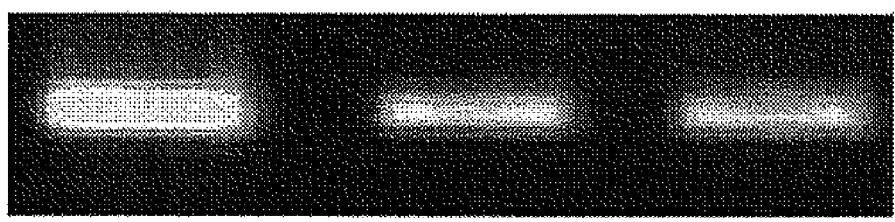
Figure 9:
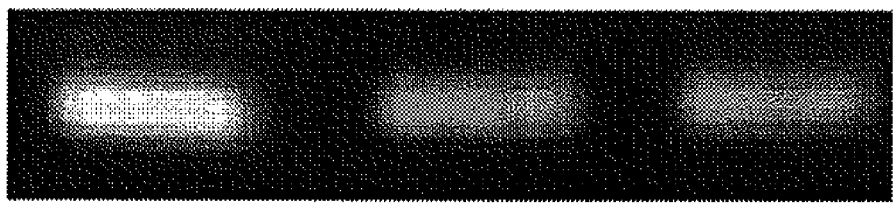
Figure 9:
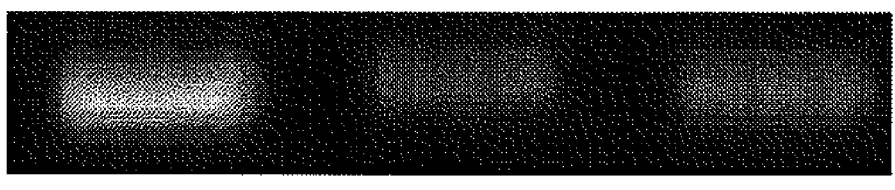

In FIG. 9, lane 1 shows products obtained after PCR with the preparative sample, lane 2 shows products obtained after PCR with the control sample, and lane 3 shows products obtained after PCR with the analytical sample. In FIG. 9, panel (a) shows products obtained after PCR with the GSTP1 primer set, panel (b) shows products obtained after PCR with the primer set 1, panel (c) shows products obtained after PCR with the primer set 2, and panel (d) shows products obtained after PCR with the primer set 3.

From the results shown in lanes 2 and 3 in panels (b) to (d) in FIG. 9, it can be seen that when the primer sets 1 to 3 are used, the amounts of the products obtained after PCR with the control sample are almost equal to the amounts of the products obtained after PCR with the analytical sample. Accordingly, it can be seen that DNA fragments which do not have a CpG site, serving as the templates for the primer sets 1 to 3, are not concentrated by immunoprecipitation of methylated DNA with an anti-methylated cytidine antibody.

Comparative Example 1

It was confirmed in Example 2 that the GAPDH gene has been methylated in the genomic DNA of MCF7 cell. Hence, it was confirmed whether the GAPDH gene was actually concentrated by immunoprecipitation of methylated DNA with an anti-methylated cytidine antibody.
Design of Primers for Amplification of the GAPDH Gene On the basis of DNA fragments obtained by treating the human genomic DNA with MseI as a restriction enzyme, a GAPDH primer set using, as a template, a methylated DNA fragment containing a nucleotide sequence of the GAPDH gene was designed. The design conditions are the same as described above in design of the primers for detection of non-methylated DNA. Primers contained in the GAPDH primer set are shown below.

```
GAPDH primer set:
GAPDH-F primer (5'-GGCACCCTATGGACACGC-3',
SEQ ID NO: 14)

GAPDH-R primer (5'-GGAAAGCCAGTCCCCAGAAC-3',
SEQ ID NO: 15)
```

PCR Using the Primer Set

By the same operation as in Example 3, PCR was conducted using the GAPDH primer set.

Figure 10:
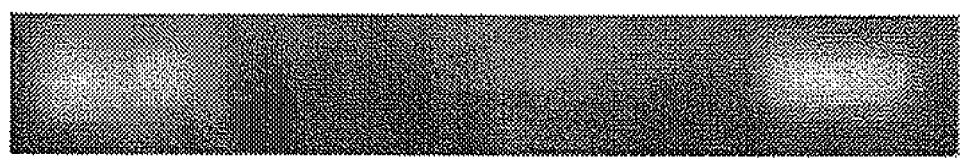
FIG. 10 is a photograph showing electrophoresis patterns of products after PCR when a GSTP1 primer set and a GAPDH primer set were used respectively.
Figure 10:
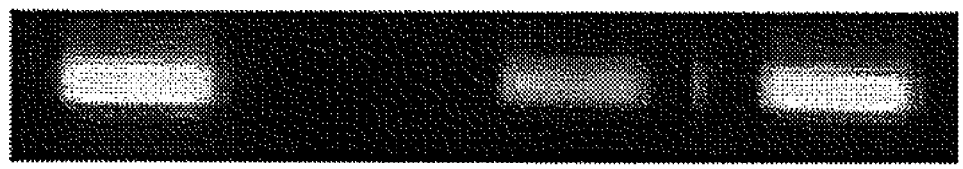

PCR was also conducted using the GSTP1 primer set as a control.
Detection of Amplified Nucleic Acid by Agarose Gel Electrophoresis The nucleic acid amplified with PCR was detected by agarose gel electrophoresis in the same manner as in Example 3. A photograph showing electrophoresis patterns after PCR with the GSTP1 primer set and GAPDH primer set is shown in FIG. 10. In FIG. 10, panel (a) shows products obtained after PCR with the GSTP1 primer set, and panel (b) shows products obtained after PCR with the GAPDH primer set.

From the results shown in lanes 2 and 3 in panel (b) in FIG. 10, it can be seen that the amounts of the products obtained after PCR using the analytical sample are higher than the amounts of the products obtained after PCR using the control sample. Accordingly, it can be seen that non-methylated DNA cannot be detected with the GAPDH primer set. The results in Comparative Example 1, along with the results in Example 2, show that the GAPDH gene that is a housekeeping gene may be inappropriate as an indicator of non-methylated DNA.

From these results, it can be seen that non-methylated DNA in the methylated DNA concentrate can be easily and accurately detected by a designed primer set like the primer sets 1 to 3.

Example 4

Preparation of a Calibration Curve of Real-Time PCR Using the GSTP1 Primer Set

Dilution series of the genomic DNA of breast cancer cell strain MCF7 were prepared. 12.5 µL of PCR reagent (trade name: 2× fast Start SYBR Green Master Mix, manufactured by Roche Diagnostics), 1 µL (10 µM) of an aqueous forward primer solution containing the GSTP1-F primer from the GSTP1 primer set, 1 µL (10 µM) of an aqueous reverse primer solution containing the GSTP1-R primer from the GSTP1 primer set, and 9.5 µL of water were added to 1 µL of the respective dilution series, to prepare reaction solutions for PCR.

The reaction solutions for PCR were used in PCR to prepare a calibration curve. PCR was conducted by incubation at 95° C. for 10 minutes and then 45 cycles of the reaction, each cycle being carried out under conditions at 95° C. for 30 seconds, at 66° C. for 15 seconds and at 72° C. for 30 seconds respectively, followed by the reaction at 95° C. for 1 minute, at 66° C. for 30 seconds and at 95° C. for 30 seconds.
Preparation of a Calibration Curve of Real-Time PCR Using the Primer Set 3

A calibration curve was prepared in the same manner as described above except that the primer set 3 was used in place of the GSTP1 primer set.
Preparation of Analytical Sample 4 µg of the genomic DNA of breast cancer cell strain MCF7 and restriction enzyme MseI (manufactured by New England Laboratory) were incubated overnight at 37° C. to obtain a sample containing DNA fragments of 300 to 1000 bp. The resulting sample containing DNA fragments was thermally denatured by incubation at 95° C. for 10 minutes to give a preparative sample. The preparative sample for use in PCR described later was also prepared in the same manner.

68 µL of buffer (trade name: ChIP dilution buffer, manufactured by Upstate Inc.) and 302 µL of Protein G beads (trade name: Protein G Sepharose beads, manufactured by GE Healthcare) were added to 4 µg of the DNA fragments after thermal denaturation, and the resulting mixture was incubated at 4° C. under stirring for 1 hour. Thereafter, a supernatant of the resulting mixture was recovered.

An anti-methylated cytidine antibody was added to the resulting supernatant, and the resulting mixture was incubated overnight at 4° C. under stirring, thereby immunoprecipitating methylated DNA.

Thereafter, an immunoprecipitation assay kit (trade name: Chromatin Immunoprecipitation Assay Kit, manufactured by Upstate Inc.) and Protein G beads (trade name: Protein G Sepharose beads, manufactured by GE Healthcare) were used to recover the DNA-antibody complex after immunoprecipitation, and the DNA was recovered from the complex.

Proteinase K (manufactured by Sigma) was added at a final concentration of 1 mg/mL to the sample containing a recovered DNA, and the resulting mixture was incubated at 50° C. for 1 hour. Thereafter, the DNA was purified from the resulting mixture by using a DNA purification kit (trade name: Qiaquick PCR purification kit, manufactured by QIAGEN), to give an analytical sample. Separately, a control sample was obtained in the same manner as described above except that an anti-mouse IgG antibody was used in place of the anti-methylated cytidine antibody. Calculation of the amount of DNA fragment serving as an indicator of methylated DNA in a sample by using the GSTP1 primer set 12.5 µL of PCR reagent (trade name: 2× fast Start SYBR Green Master Mix, manufactured by Roche Diagnostics), 1

μL (10 μM) of an aqueous forward primer solution containing the GSTP1-F primer from the GSTP1 primer set, 1 μL (10 μM) of an aqueous reverse primer solution containing the GSTP1-R primer from the GSTP1 primer set, and 9.5 μL of water were added to 1 μL of the analytical sample to prepare a reaction solution for PCR. The reaction for PCR was used in PCR. Separately, PCR using the preparative sample and the control sample as controls was conducted. PCR was conducted by incubation at 95° C. for 10 minutes and then 45 cycles of the reaction, each cycle being carried out under conditions at 95° C. for 30 seconds, at 66° C. for 15 seconds and at 72° C. for 30 seconds respectively, followed by the reaction at 95° C. for 1 minute, at 66° C. for 30 seconds and at 95° C. for 30 seconds.

On the basis of the results in this PCR and the calibration curve described above, the amounts of GSTP1 DNA (DNA fragment serving as an indicator of methylated DNA) contained in the preparative sample, the analytical sample and the control sample respectively were calculated. Hereinafter, the DNA fragment serving as an indicator of methylated DNA is referred to simply as methylated DNA fragment.

Calculation of the Amount of DNA Fragment Serving as an Indicator of Non-Methylated DNA in a Sample by Using the Primer Set 3

The amounts of the DNA fragment serving as an indicator of non-methylated DNA contained in the preparative sample, the analytical sample and the control sample were calculated by using the primer set 3 in place of the GSTP1 primer set. Hereinafter, the DNA fragment serving as an indicator of non-methylated DNA is referred to simply as non-methylated DNA fragment.

Evaluation of the Purity of the Methylated DNA Concentrate (Analytical Sample)

On the basis of the calculated amounts of the methylated DNA fragment and the non-methylated DNA fragment, the ratio of methylated DNA/non-methylated DNA in the preparative sample, the control sample or the analytical sample was calculated according to the following equation (4):

$$\text{Methylated DNA/non-methylated DNA ratio (ng/ng)} = \text{Amount (ng) of methylated DNA/amount (ng) of non-methylated DNA} \quad (4)$$

Figure 11:
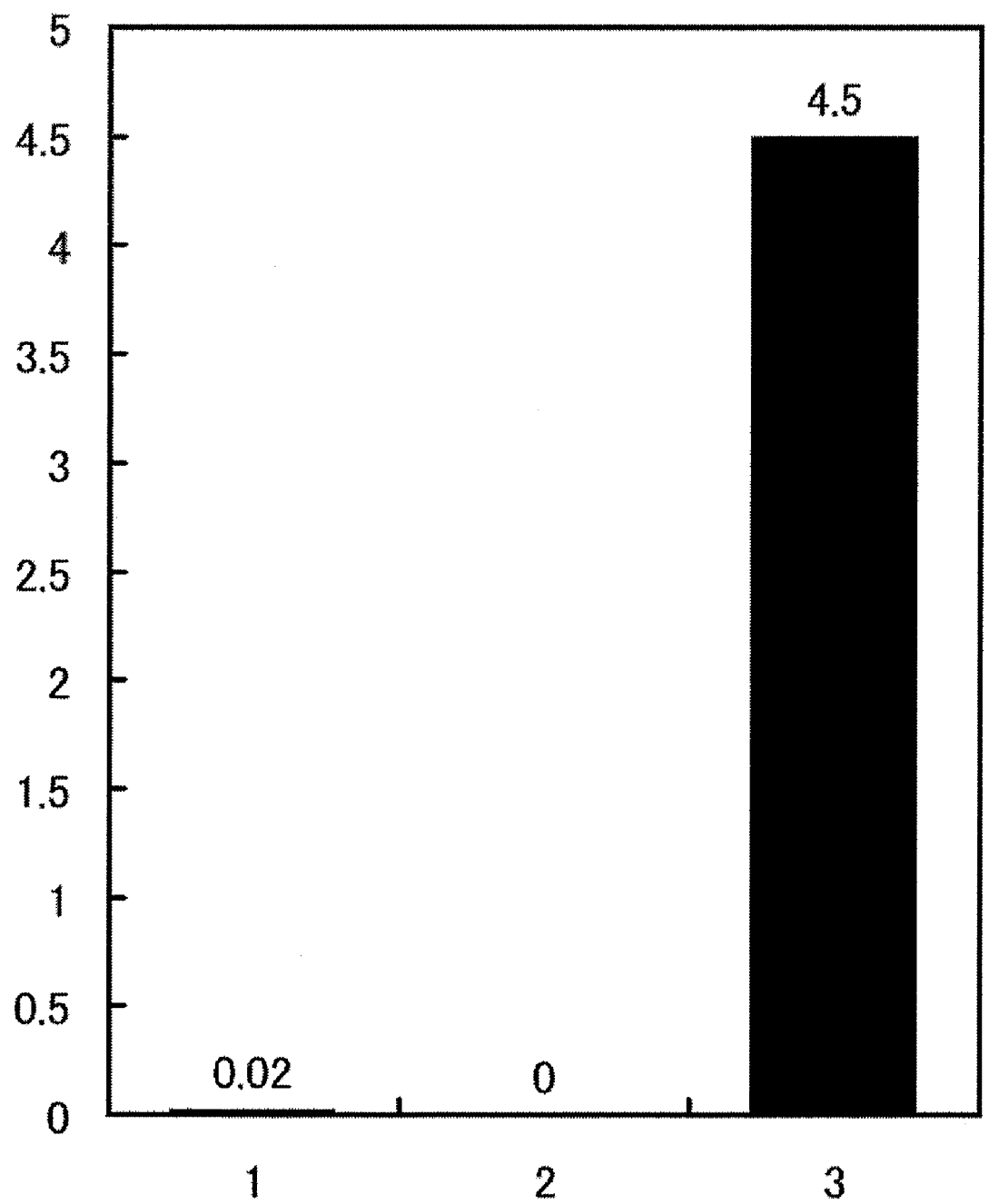
FIG. 11 is a graph showing proportions of methylated DNA and non-methylated DNA in a sample.

FIG. 11 shows a graph showing the ratio of methylated DNA/non-methylated DNA in the sample. In FIG. 11, lane 1 shows the ratio of methylated DNA/non-methylated DNA in the preparative sample. Lane 2 shows the ratio of methylated DNA/non-methylated DNA in the control sample. Lane 3 shows the ratio of methylated DNA/non-methylated DNA in the analytical sample.

From the results shown in FIG. 11, it can be seen that the ratio of methylated DNA/non-methylated DNA in the preparative sample is 0.02 ng/ng, and the ratio of methylated DNA/non-methylated DNA in the control sample is 0.07 ng/ng. It can also be seen that the ratio of methylated DNA/non-methylated DNA in the analytical sample subjected to immunoprecipitation with an anti-methylated cytidine antibody is 4.5 ng/ng. From these results, it can be seen that as compared with the preparative sample and control sample, the analytical sample that is a methylated DNA concentrate had a higher ratio of GSTP1 DNA that is methylated DNA.

Example 5

The ratio of methylated DNA/non-methylated DNA in the analytical sample (methylated DNA concentrate) and the ratio of methylated DNA/non-methylated DNA in the control sample or preparative sample, calculated in Example 4, can be used to calculate the concentration rate of methylated DNA. The concentration rate can be calculated for example according to the following equation (5):

$$\text{Concentration rate of methylated DNA} = \text{[methylated DNA/non-methylated DNA ratio (ng/ng) in the analytical sample]/[methylated DNA/non-methylated DNA ratio (ng/ng) in the preparative sample]}$$

From the results in Example 4, the methylated DNA/non-methylated DNA ratio (ng/ng) in the analytical sample is 4.5 (ng/ng), while the methylated DNA/non-methylated DNA ratio (ng/ng) in the preparative sample is 0.02 (ng/ng). Accordingly, the concentration rate of methylated DNA in the analytical sample, as calculated using the equation (5), is 225-fold. The methylated DNA/non-methylated DNA ratio (ng/ng) in the control sample can also be used in place of the methylated DNA/non-methylated DNA ratio (ng/ng) in the preparative sample.

From the above results, it was suggested that the primer set 3 that is the primer set of the present invention, and the GSTP1 primer set that is a primer set using a methylated DNA fragment as a template, can be used to evaluate the purity of a methylated DNA concentrate and to calculate the concentration rate of a methylated DNA concentrate.

Example 6

Non-methylated DNA in a methylated DNA concentrate was detected with the primer set 2 in the same operation as in Example 3 except that genomic DNA of breast cancer cell strain MDA231 was used in place of the genomic DNA of the breast cancer cell strain MCF7.

It is known that in the genomic DNA of the breast cancer cell strain MDA231, a promoter region of CDH1 gene is methylated. Accordingly, a CDH1 promoter set using, as a template, a DNA fragment containing a nucleotide sequence of the promoter region of CDH1 gene, out of DNA fragments obtained by treating the human genomic DNA with MseI as a restriction enzyme, was used as the primers for detection of methylated DNA. Conditions for designing the CDH1 primer set are the same as in designing the primers for detection of non-methylated DNA in Example 3. Primers contained in the GSTP1 primer set are shown below.

```
GSTP1 primer set:
CDH1-F primer (5'-GTGAACCCTCAGCCAATCAG-3',
SEQ ID NO: 18)

CDH1-Rv primer (5'-AGTTCCGACGCCACTGAG-3',
SEQ ID NO: 19)
```

Figure 12:
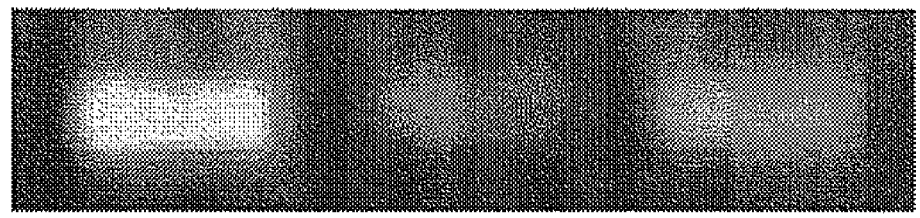
FIG. 12 is a photograph showing electrophoresis patterns of products after PCR when a primer set 2 and a CDH1 primer set were used respectively.
Figure 12:
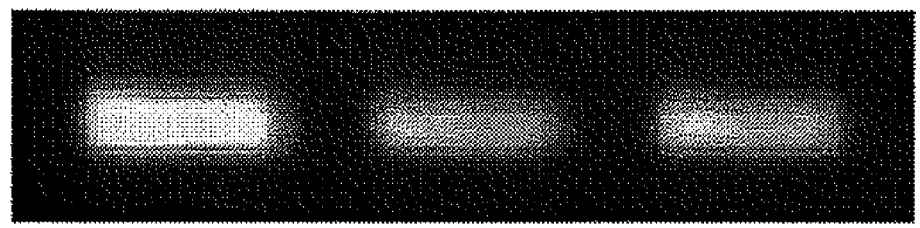

A photograph showing electrophoresis patterns of products obtained after PCR using the primer set 2 and the CDH1 primer set respectively is shown in FIG. 12. In FIG. 12, lane 1 shows a product obtained after PCR with the preparative sample, lane 2 shows a product obtained after PCR with the control sample, and lane 3 shows a product obtained after PCR with the analytical sample (methylated DNA concentrate). In FIG. 12, panel (a) shows products obtained after PCR with the CDH1 primer set, and panel (b) shows products obtained after PCR with the primer set 2.

From the results shown in FIG. 12, it can be seen that when the primer set 2 is used, the amount of the product obtained after PCR with the control sample is almost equal to the amount of the product obtained after PCR with the analytical sample. It can also be seen that when the CDH1 primer set is used, the amount of the product obtained after PCR using the analytical sample is higher than the amount of the product obtained after PCR with the control sample. From this result, it was suggested that regardless of the type of cancer cell, methylated DNA in the methylated DNA concentrate can be detected by using the primer set 2, that is, the primer set of the present invention.

Example 7

Non-methylated DNA in a methylated DNA concentrate was detected with the primer set 1 and GSTP1 primer set in the same operation as in Example 3 except that genomic DNA of normal mammary gland epithelial cell HMEC was used in place of the genomic DNA of the breast cancer cell strain MCF7. It is known that in the genomic DNA of the normal mammary gland epithelial cell, a promoter region of GSTP1 gene is not methylated.

Figure 13:
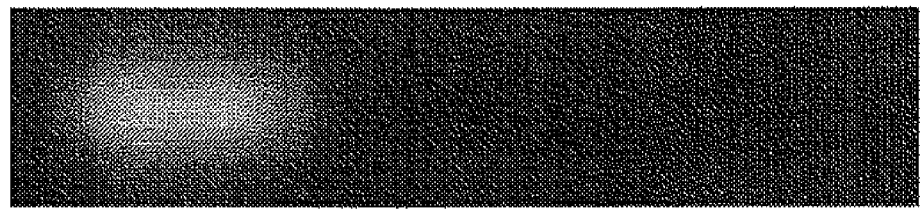
FIG. 13 is a photograph showing electrophoresis patterns of products after PCR when a primer set 1 and a GSTP1 primer set were used respectively.
Figure 13:
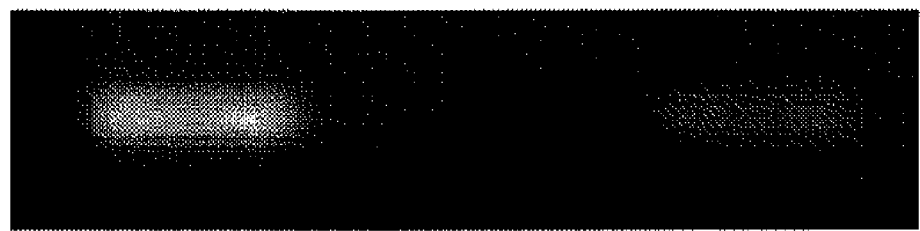

A photograph showing electrophoresis patterns of products after PCR using the primer set 1 and the GSTP1 primer set respectively is shown in FIG. 13. In FIG. 13, lane 1 shows products obtained after PCR with the preparative sample, lane 2 shows products obtained after PCR with the control sample, and lane 3 shows products obtained after PCR with the analytical sample (methylated DNA concentrate). In FIG. 13, panel (a) shows products obtained after PCR with the GSTP1 primer set, and panel (b) shows products obtained after PCR with the primer set 1.

From the results shown in lanes 2 and 3 in FIG. 13, it can be seen that the amount of the product obtained after PCR with the control sample and the amount of the product obtained after PCR with the analytical sample (methylated DNA concentrate) are almost the same regardless of whether the primer set 1 or the GSTP1 primer set is used. From this result, it was suggested that methylated DNA in the methylated DNA concentrate prepared from the normal cell can also be detected with the primer set 1, that is, the primer set of the present invention.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A method of analyzing methylated DNA, comprising steps of:
    treating a DNA-containing sample with a restriction enzyme to obtain a sample containing a DNA fragment;
    concentrating methylated DNA contained in the sample obtained in the treating step to obtain a methylated DNA concentrate;
    subjecting the methylated DNA concentrate to nucleic acid amplification reaction, using a primer set for amplifying non-methylated DNA which the methylated DNA concentrate may comprise;
    detecting an amplification product obtained by the nucleic acid amplification reaction;
    judging whether amplification product detected in the detecting step is not higher than a predetermined amount; and
    analyzing the methylated DNA contained in the methylated DNA concentrate when the amplification product is not higher than the predetermined amount.

2. The method according to claim 1, wherein the restriction enzyme recognizes 4 to 6 bases.

3. The method according to claim 1, wherein the restriction enzyme recognizes a nucleotide sequence which does not have a CpG site to cleave its cleavage site.

4. The method according to claim 1, wherein the restriction enzyme is MseI.

5. The analysis method according to claim 1, wherein in the concentrating step, the methylated DNA is concentrated with an anti-methylated cytosine antibody, an anti-methylated cytidine antibody or a methylated DNA-binding protein.

6. The method according to claim 1, wherein the DNA-containing sample comprises DNA prepared from a cancer cell.

7. A method of judging a reliability of an analysis result of methylated DNA, comprising steps of:
    treating a DNA-containing sample with a restriction enzyme to obtain a sample containing a DNA fragment;
    concentrating methylated DNA contained in the sample obtained in the treating step to obtain a methylated DNA concentrate;
    subjecting the methylated DNA concentrate to nucleic acid amplification reaction using a primer set for amplifying non-methylated DNA which the methylated DNA concentrate may comprise;
    detecting an amplification product obtained by the nucleic acid amplification reaction;
    analyzing the methylated DNA contained in the methylated DNA concentrate; and judging the reliability of the analysis result of the methylated DNA in the analyzing step, on the basis of the detection result of the amplification product in the detecting step.

8. The method according to claim 7, wherein the restriction enzyme recognizes 4 to 6 bases.

9. The method according to claim 7, wherein the restriction enzyme recognizes a nucleotide sequence which does not have a CpG site to cleave its cleavage site.

10. The method according to claim 7, wherein the restriction enzyme is MseI.

11. The method according to claim 7, wherein, in the judging step, the analysis result is judged to be low in reliability in the case that the amplification product detected in the detecting step is higher than a predetermined amount, and the analysis result is judged to be high in reliability in the case that the detection result of the amplification product is not higher than the predetermined amount.

12. A method of calculating of a concentration rate of methylated DNA, comprising steps of:
    treating a DNA-containing sample with a restriction enzyme to obtain a sample containing a DNA fragment;
    concentrating methylated DNA contained in the sample obtained in the treating step to obtain a methylated DNA concentrate;
    performing the following nucleic acid amplification reactions (i) to (iv):
        (i) nucleic acid amplification reaction using the methylated DNA concentrate obtained in the concentrating step and a primer set for amplifying non-methylated DNA which the methylated DNA concentrate may comprise;
        (ii) nucleic acid amplification reaction using the methylated DNA concentrate obtained in the concentrating step and a primer set for amplifying the methylated DNA;
        (iii) nucleic acid amplification reaction using the sample containing the DNA fragment obtained in the treating step and a primer set for amplifying non-methylated DNA which the methylated DNA concentrate may comprise; and
        (iv) nucleic acid amplification reaction using the sample containing the DNA fragment obtained in the treating step and a primer set for amplifying the methylated DNA;
    measuring amounts of the amplification products obtained by the nucleic acid amplification reactions (i) to (iv); and
    calculating the concentration rate of the methylated DNA on the basis of the amounts of the amplification products measured in the measuring step.

13. The method according to claim 12, wherein the concentration rate is calculated according to the following equation:

the concentration rate=[the amount of amplification product obtained by nucleic acid amplification (ii)/the amount of amplification product obtained by nucleic acid amplification reaction (i)]/[the amount of amplification product obtained by nucleic acid amplification reaction (iv)/the amount of amplification product obtained by nucleic acid amplification reaction (iii)].

14. A method of evaluating a purity of a methylated DNA concentrate, comprising steps of:
    treating a DNA-containing sample with a restriction enzyme to obtain a sample containing a DNA fragment;
    concentrating methylated DNA contained in the sample obtained in the training step to obtain a methylated DNA concentrate;
    performing the following nucleic acid amplification reactions (i) and (ii):
        (i) nucleic acid amplification reaction using the methylated DNA concentrate and a primer set for amplifying non-methylated DNA which the methylated DNA concentrate may comprise; and
        (ii) nucleic acid amplification reaction using the methylated DNA concentrate and a primer set for amplifying the methylated DNA;
    measuring amounts of the amplification products obtained by the nucleic acid amplifications (i) and (ii); and
    evaluating the purity of the methylated DNA concentrate, on the basis of the amounts of the amplification products measured in the measuring step.

15. The method according to claim 14, wherein, in the evaluating step, the purity of the methylated DNA concentrate is evaluated to be high in the case that a value obtained by dividing the amount of the amplification product obtained by the nucleic acid amplification reaction (ii) by the amount of the amplification product obtained by the nucleic acid amplification reaction (i) is higher than a predetermined value, and the purity of the methylated DNA concentrate is evaluated to be low in the case that a value obtained by dividing the amount of the amplification product obtained by the nucleic acid amplification reaction (ii) by the amount of the amplification product obtained by the nucleic acid amplification reaction (i) is not higher than the predetermined value.

\* \* \* \* \*

SEQUENCE LISTING

```
<160> NUMBER OF SEQ ID NOS: 19

<210> SEQ ID NO 1
<211> LENGTH: 341
<212> TYPE: DNA
<213> ORGANISM: Artificial sequence
<220> FEATURE:
<223> OTHER INFORMATION: A target sequence for a primer set

<400> SEQUENCE: 1
ttaagttgct aagttttggg aaaatttgct atacaaatag ataaccagaa caaggacaaa      60
aaggaggagt caagagaagt tggaagccaa ctgagagaga gggaaggctt gaagtggtca     120
ggacagtgaa cacctaagag acatccactg aatttgccca ctaggaagcc attagtgact     180
tcaataggaa catcttcagt gcatcatgaa ggccaaagat tgccatgaaa gagaggaatg     240
gaaatggagt gtgggccact ttttcaataa gcttggccat gaaacaaggg acagaaacag     300
tggaaattag atggagatgc aaagtcaaaa tttttcttta a                         341

<210> SEQ ID NO 2
<211> LENGTH: 364
<212> TYPE: DNA
<213> ORGANISM: Artificial sequence
<220> FEATURE:
<223> OTHER INFORMATION: A target sequence for a primer set

<400> SEQUENCE: 2
ttaaggttag aaatgagtca tttgtactta gttaaagaag agaagggtac tttgccaata      60
tagccatgca gctattctga atctgaaact gttcccagac ataaggttta tgagtgctaa     120
gacatctgag ctgttctccc tcccacttag ccaagccccc ggttctgcct cacttccagg     180
aaccctctcc tggtgcatgc atgtcagata aaagtctgaa agtgatgagt tacattacca     240
ccatttctca atactttgaa gaaaaaaata tctaaaagat ttcacagtgg ttggtcactt     300
ttcatattat tatgaactga aatgcaactt tgcacacaca atatttttga agatatatat     360
ttaa                                                                  364

<210> SEQ ID NO 3
```

-continued

```
<211> LENGTH: 238
<212> TYPE: DNA
<213> ORGANISM: Artificial sequence
<220> FEATURE:
<223> OTHER INFORMATION: A target sequence for a primer set

<400> SEQUENCE: 3
ttaaaggatg ggagacacct ggttcatttc tcatgcaaat gagaaagaca ctgcattcac      60
aagggagagt ggctgacagt ataggagtga agggcaaaaa gctagagaga agaggaggat    120
gggatccaga cctcagactg agtacaaagc agctggtcca tcccatattt gactgctcct    180
agatatttta gtagctctgg aaagttggtg atgagaaaga tggtttactc ctacttaa     238

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 4
ggaggagtca agagaagttg gaagc                                           25

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 5
cccacactcc atttccattc ctc                                             23

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 6
gggtactttg ccaatatagc catgc                                           25

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 7
tggctaagtg ggagggagaa cag                                             23

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 8
ggatgggaga cacctggttc a                                               21

<210> SEQ ID NO 9
<211> LENGTH: 24
<212> TYPE: DNA
```

-continued

<213> ORGANISM: Artificial sequence
<220> FEATURE:
<223> OTHER INFORMATION: Synthetic oligonucleotide primer

<400> SEQUENCE: 9
ggatggacca gctgctttgt actc                                          24

<210> SEQ ID NO 10
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 10 gagattttt taaaattaag tgggg                                          25

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 11
ataaaaaaac caatccccaa aac                                           23

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 12
tagaggggtg atgtggggag ta                                            22

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 13
ctaaccccaa ccacatacca aaa                                           23

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 14
ggcaccctat ggacacgc                                                 18

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 15
ggaaagccag tccccagaac                                               20

```
<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 16
gaggccttcg ctggagtt                                                 18

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 17
gtactcactg gtggcgaaga                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 18
gtgaaccctc agccaatcag                                               20

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 19
agttccgacg ccactgag                                                 18
```